United States Patent
Majumder et al.

(10) Patent No.: US 9,193,642 B2
(45) Date of Patent: Nov. 24, 2015

(54) PROCESS FOR PRODUCTION OF DIALKYLBENZENES

(71) Applicant: UOP LLC, Des Plaines, IL (US)

(72) Inventors: Debarshi Majumder, Forest Park, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 104 days.

(21) Appl. No.: 13/923,166

(22) Filed: Jun. 20, 2013

(65) Prior Publication Data

US 2014/0378723 A1 Dec. 25, 2014

(51) Int. Cl.
| | |
|---|---|
| C07C 2/66 | (2006.01) |
| C07C 2/86 | (2006.01) |
| C07C 5/03 | (2006.01) |
| C07C 5/327 | (2006.01) |
| C07C 7/148 | (2006.01) |

(52) U.S. Cl.
CPC . *C07C 2/66* (2013.01); *C07C 2/867* (2013.01); *C07C 5/03* (2013.01); *C07C 5/327* (2013.01); *C07C 7/14891* (2013.01)

(58) Field of Classification Search
USPC .................................................. 585/449, 467
See application file for complete search history.

(56) References Cited

U.S. PATENT DOCUMENTS

| | | | |
|---|---|---|---|
| 4,260,843 A | 4/1981 | Chu | |
| 4,276,437 A | 6/1981 | Chu | |
| 4,349,461 A | 9/1982 | Chu et al. | |
| 4,357,264 A | 11/1982 | Chu | |
| 4,374,045 A | 2/1983 | Chu | |
| 4,384,155 A | 5/1983 | Chu | |
| 4,399,059 A | 8/1983 | Chu | |
| 4,447,666 A | 5/1984 | McWilliams | |
| 4,472,518 A | 9/1984 | Chu | |
| 4,532,226 A | 7/1985 | Chu | |
| 4,581,215 A | 4/1986 | Kaeding | |
| 6,627,781 B1 * | 9/2003 | Briot et al. | 585/449 |
| 7,361,798 B2 | 4/2008 | Clark et al. | |
| 8,329,966 B2 | 12/2012 | Tsai et al. | |
| 2004/0030211 A1 | 2/2004 | Chi et al. | |
| 2008/0194895 A1 * | 8/2008 | Sohn et al. | 585/435 |

FOREIGN PATENT DOCUMENTS

JP 60105635 A2 6/1985

OTHER PUBLICATIONS

Ren et al., "Preparation and Properties of Dialkylbenzene as Lubricating Oil," Shiyou Xuebao, Shiyou Jiagong (1990), 6(1), 76-83.

* cited by examiner

*Primary Examiner* — Thuan D Dang

(57) ABSTRACT

A method of making dialkylaromatics as a primary product is described. The design involves a dual reaction zone system, both reaction zones containing alkylation catalysts. The olefin feed is split into two portions (or two feeds are used), the first portion being fed to a first alkylation reaction zone and reacted with a first olefin. The other portion of olefin is reacted in a second reaction zone with the linear alkylaromatics formed in the first reaction zone to form the dialkylaromatics.

4 Claims, 2 Drawing Sheets

PROCESS FOR PRODUCTION OF DIALKYLBENZENES

BACKGROUND OF THE INVENTION

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes have been manufactured commercially using Friedel-Crafts condensation employing catalysts such as aluminum chloride, or by using strong acid catalysts such as hydrogen fluoride, for example, to alkylate benzene with olefins. In 1995, a solid bed alkylation process, the Detal™ process, using a solid non-corrosive acid catalyst was introduced.

Current LAB manufacturing processes employing solid alkylation catalysts use kerosene-based $C_9$ to $C_{16}$ material from a Pacol™ dehydrogenation process, which is typically a mixture of about 9-15% olefins in paraffin.

Gas-to-liquid (GTL) technologies for the generation of $C_9$ to $C_{16}$ range of hydrocarbons have raised interest in the possibility of producing LAB using a GTL-based feed source. The ability to use a GTL feedstock would reduce dependence on crude-based feedstocks.

Dialkylbenzenes made from $C_{10}$ to $C_{13}$ olefins and benzene have been recognized as promising candidates in tertiary oil recovery applications and for use as lubricants. Demand for dialkylbenzenes has been steadily increasing in recent years.

Currently, there is no commercial process to make dialkylbenzenes as a primary product. They are presently produced in small quantities as a side reaction in the manufacture of linear alkylbenzenes. The typical ratio of dialkylbenzenes: linear alkyl benzenes in a linear alkylbenzene complex is about 1-5 wt %, which is too low to support the increasing demand for dialkylbenzenes in the face of relatively steady demand for linear alkylbenzenes.

Thus, there exists a need for methods for making dialkylbenzenes.

SUMMARY OF THE INVENTION

One aspect of the invention is a process the production of dialkylaromatics. In one embodiment, the process involves contacting an aromatic compound, and a first feed comprising a first olefin and a first component in a first alkylation reaction zone under alkylation conditions in the presence of a first alkylation catalyst to produce a first effluent containing monoalkylaromatics. The monoalkylaromatics are separated from the first effluent and contacted with a second feed comprising a second olefin and a second component in a second alkylation reaction zone under alkylation conditions in the presence of a second alkylation catalyst to produce a second effluent containing dialkylaromatics. The dialkylaromatics are separated from the second effluent. Neither the first nor the second catalyst is $AlCl_3$.

DETAILED DESCRIPTION OF THE INVENTION

Figure 1:
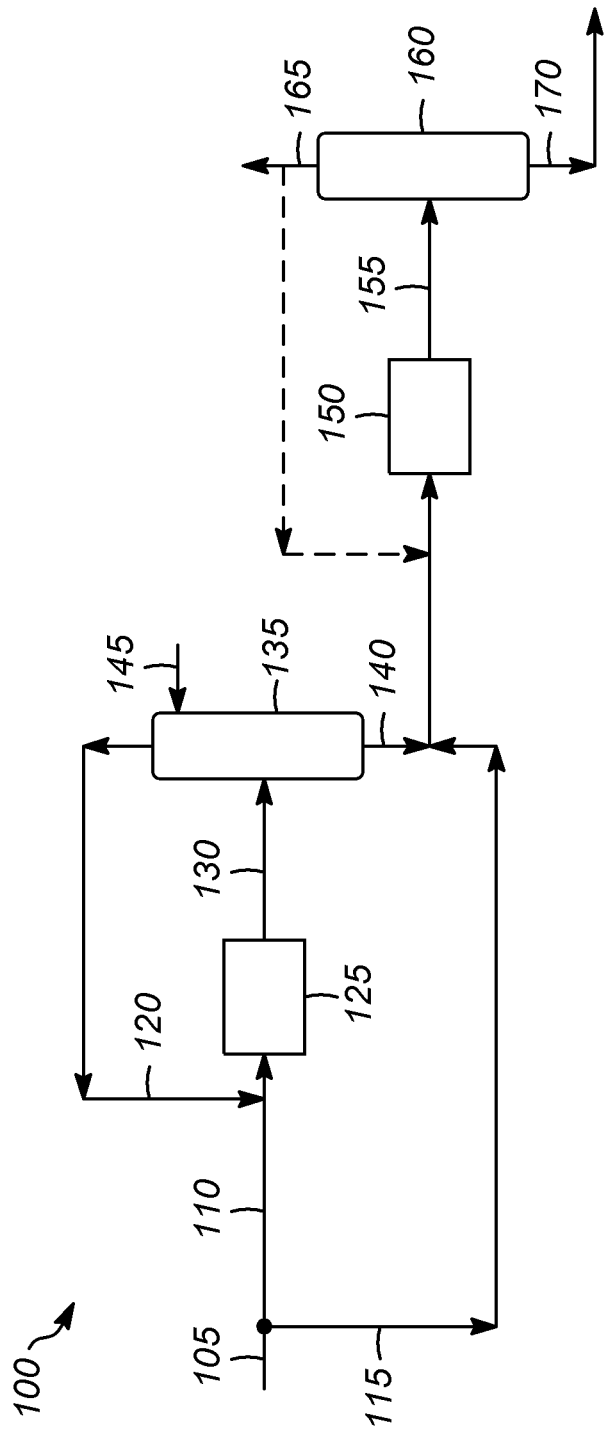
FIG. 1 is an illustration of one embodiment of a process for making dialkylbenzenes.

The present invention provides a method of making dialkylaromatics as a primary product. The design involves a dual reaction zone system, both reaction zones containing alkylation catalysts. The olefin feed is split into two portions (or two feeds are used), the first portion being fed to a first alkylation reaction zone and reacted with a first olefin. The other portion of olefin is reacted in a second reaction zone with the linear alkylaromatics formed in the first reaction zone to form the dialkylaromatics.

The two reaction zones can be in the same reactor vessel, or in separate reactor vessels. Because the second catalyst may reach the end of its life before the first catalyst, having separate reactor vessels may be advantageous in terms of reloading the catalyst. In some embodiments, the second reactor may be operated at higher temperature to obtain complete conversion depending on the molar ratio of linear alkylaromatics to olefins used. Each reactor may include one or more catalyst beds.

The aromatic compound used in the dialkylation process can be any suitable aromatic compound, including, but not limited to, benzene, toluene, ethylbenzene, xylenes, or combinations thereof. Benzene is the most commonly used aromatic compound. Consequently, benzene will be used for ease of discussion.

The aliphatic feedstock used in the alkylation processes of this invention contains aliphatic mono-olefin of 9 to 17, or 10 to 13, or 14 to 17 carbon atoms per molecule. The aliphatic olefin is usually a mixture of olefins having different molecular weights. The olefin may be an alpha-olefin or comprise a mixture of olefin isomers. In most instances, the positioning of the olefinic bond in the molecule is not critical as most solid alkylation catalysts have been found to promote migration of the olefinic bond.

For commercial processes, other components may be present in the aliphatic feedstock with the olefin-containing aliphatic compound. These other components may comprise paraffins of 9 to 17, or 10 to 13, or 14 to 17 carbon atoms per molecule. However, such amounts of paraffin are not critical to the processes of this invention, and aliphatic feedstocks having an essential absence of paraffins can be used. If paraffins are not present, then another component that can act a heat sink and remains unreacted under the process conditions will need to be present to maintain the LAB linearity and 2-phenyl content, if that is needed for the particular application.

Generally, depending on the reservoir characteristics, there may be an optimum specification of the alkaline/surfactant/polymer (ASP) mixture for enhancing the tertiary oil recovery efficiency. Of particular importance are characteristics such as interfacial tension, viscosity and density of this mixture. Depending on the linearity and 2-phenyl specifications of the dialkylbenzene-sulfonate, these properties are different.

Suitable sources for the aliphatic feedstock include, but are not limited to, a feed from the Pacol™ dehydrogenation process (9-15% olefins), or the product of the GTL process (e.g., about 25% olefins and 75% paraffins).

One embodiment of the process 100 is shown in the Figure. A paraffin and olefin feed 105 is split into two portions 110 and 115. Portion 110 is mixed with benzene 120 and sent to the first reaction zone 125. The effluent 130 from the first reaction zone contains monoalkylbenzenes, as well as unreacted benzene. The effluent 130 is sent to a separation zone 135 where the unreacted benzene 120 is separated from the monoalkylbenzenes and unreacted paraffins 140. Makeup benzene 145 can be added to the separation zone 135 or to the recycle benzene (not shown).

The monoalkylbenzenes and unreacted paraffins 140 are mixed with the second portion 115 of the feed 105 and sent to a second reaction zone 150. The effluent 155 from the second reaction zone 150 includes dialkylbenzenes and unreacted paraffins. The effluent 155 from the second reaction zone 150 is sent to a second separation zone 160 where the unreacted paraffins 165 are separated from the dialkylbenzenes 170. A portion of the unreacted paraffins 165 can optionally be recycled and mixed with the mixture of the first reactor effluent 140 and the second portion 115 of the feed 105, if desired.

In some embodiments, the olefin is split between the two reaction zones such that the linear alkylbenzenes and olefins are introduced in each bed in stoichiometric amounts. This eliminates the need to have a separate heavy alkylate distillation column.

Figure 2:
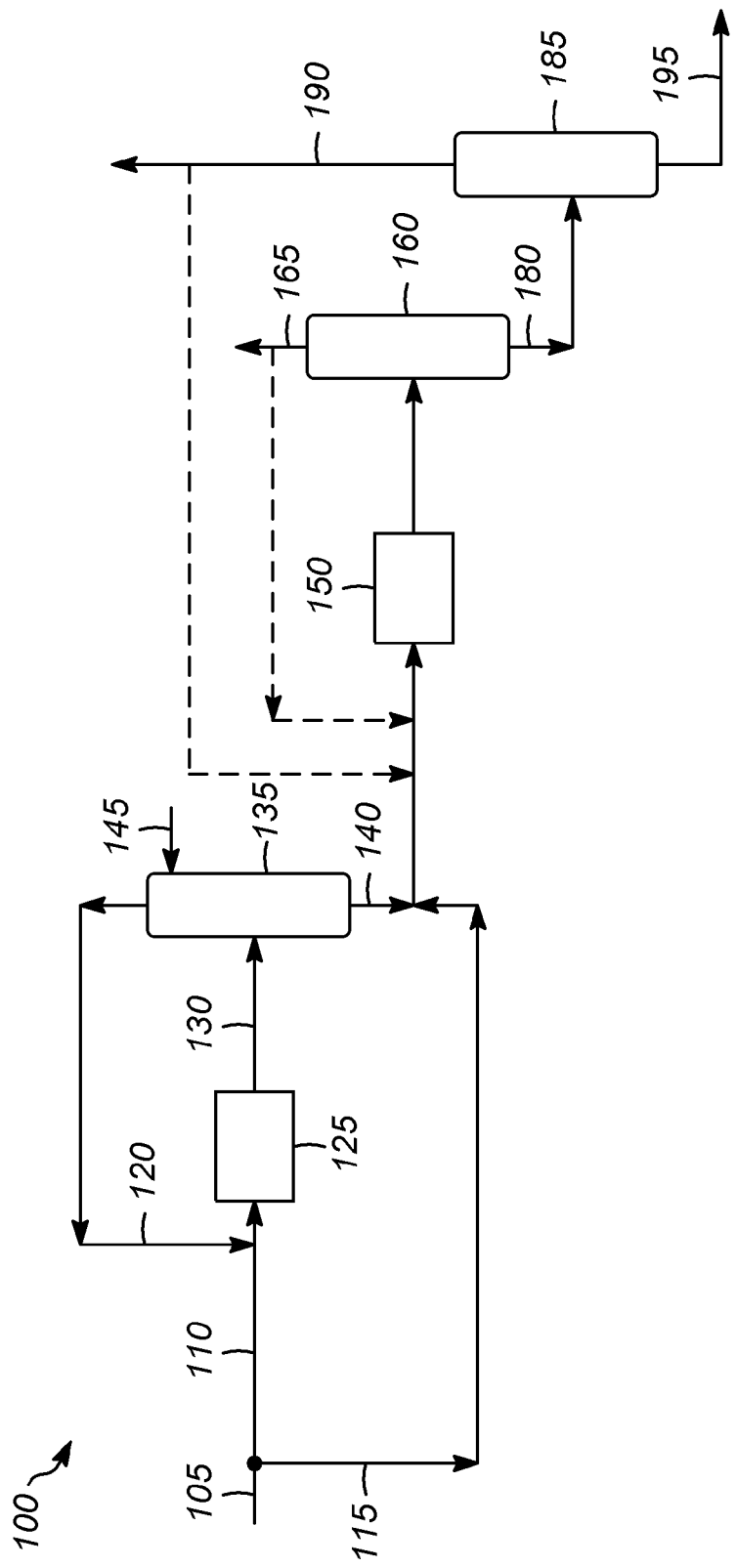
FIG. 2 is an illustration of another embodiment of a process for making dialkylbenzenes.

In other embodiments, the conversion of monoalkylbenzenes in the second reaction zone is not complete, and there are unreacted monoalkylbenzenes in the effluent. As shown in FIG. 2, the effluent 180 from the second separation zone 160 is sent to a separation zone 185 where the unreacted monoalkylbenzenes 190 are separated from the dialkylbenzenes 195. The unreacted monoalkylbenzenes 190 can optionally be recycled to the second reaction zone 150. In some embodiments, the monoalkylbenzene conversion in the second reaction zone 150 is no more than about 95%. This reduces the likelihood of forming trialkylbenzenes if the trialkylbenzenes are not sterically hindered by the catalyst employed in this section.

In other embodiments, rather than splitting the feed, there could be two separate feeds with the same or different compositions.

The optional paraffin recycle can be used to dilute the concentration of dialkylbenzenes in the second reaction zone. If the catalyst in the second reactor has a small pore size, it will be subject to faster deactivation. The paraffin recycle can be used to slow the rate of deactivation.

The molar ratio of benzene to olefin can be varied depending on the catalyst employed. For example, amorphous Si—Al based catalyst has been found to be stable with a benzene to olefin ratio greater than about 10, while zeolitic catalysts have been found to be stable at a benzene to olefin ratio greater than about 2. The molar ratio of benzene to olefin is typically between about 3 and about 30.

The aromatic compound and the olefin are reacted under alkylation conditions in the presence of a solid alkylation catalyst. These alkylation conditions generally include a temperature in the range between about 80° C. and about 200° C., most usually at a temperature not exceeding about 175° C., e.g., 100° C. to 160° C. Typically, as the catalyst ages, the temperature of the alkylation is increased to maintain desired activity. The alkylation is an exothermic reaction, and thus, in a substantially adiabatic reactor, the effluent is at a higher temperature than that of the feed (Reaction Zone Delta T). A substantially adiabatic reactor is one where the increase in temperature of the effluent over that of the feed accounts for at least about 75 percent of heat generated by the reactions in the reaction zone.

Typically, the temperature within a reaction zone has been maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in negative effects not only in terms of catalyst deactivation, but also in terms of product quality degradation, especially skeletal isomerization, and, in particular, skeletal isomerization of the olefin.

If the linearity of the dialkylbenzenes is important, the ratio of aromatic to aliphatic feedstock fed to each reaction zone in accordance with the processes of this invention can be selected such that the Reaction Zone Delta T is less than about 15° C., or less than about 12° C., or less than about 10° C., or between about 2° C. to 10° C. Desirably, the amount of aliphatic feedstock to each reaction zone is such that no reaction zone has a Reaction Zone Delta T greater than about 5° C. more than any other reaction zone. Desirably, the difference in the Reaction Zone Delta T among the reaction zones is less than about 5° C.

The use of a paraffin stream can slow the extent of skeletal isomerization of the olefins, leading to a more linear dialkylbenzene product.

Since the alkylation is typically conducted in the presence of a liquid phase, and preferably in either an all-liquid phase or at supercritical conditions, pressures must be sufficient to maintain reactants in the liquid phase. The requisite pressure necessarily depends upon the olefin and temperature, but normally is in the range of about 1300 to 7000 kPa(g), and most usually between about 2000 and 3500 kPa(g).

In some embodiments, alkylation of benzene by the olefins is conducted in a continuous manner. For purposes herein, a catalyst bed is termed a reaction zone whether in the same or a separate vessel from another bed. Each reaction zone has an inlet region and an outlet region. The reactants may be in admixture prior to entering the inlet region of the reaction zone, or they may be individually introduced and mixed in the reaction zone.

The catalyst may be used as a packed bed, a moving bed, or a slurry bed. The feed to the reaction zone may be passed either upflow or downflow, or even horizontally as in a radial bed reactor; however, the flows of the aromatic compound and olefin are co-current. In one desirable variant, olefin may be fed into several discrete points within the reaction zone. The feed mixture, that is, aromatic compound and aliphatic feedstock to a reaction zone, is often provided at an overall liquid hourly space velocity (overall LHSV) between about 0.3 and about 6 or 10 hr$^{-1}$, and most frequently between about 0.4 and 6 hr$^{-1}$ depending upon, e.g., alkylation temperature and the activity of the catalyst. The overall LHSV is determined from the LHSV's of each of the beds. The reciprocal of the overall LHSV is the sum of the reciprocals of the LHSV of each of the beds in series.

It is usually desired that sufficient residence time in the reaction zone be used such that at least about 90, or at least about 95, or at least about 98, and often at least about 99.5, mass percent of the olefin fed to a reaction zone is reacted in that reaction zone.

Any suitable solid alkylation catalyst may be used in the present invention, provided that the requirements for conversion, selectivity, and activity are met. The same or different catalyst may be in each reaction zone of the alkylation reactor assembly.

When a catalyst is used that does not favor the formation of tri-alkylaromatics, a stoichiometric or near stoichiometric ratio of linear alkylaromatics to olefins can be used (e.g., about 1:1 to about 2:1), which reduces or eliminates the need to recirculate linear alkylaromatics. Reduction or elimination of the linear alkylaromatics recycle may allow elimination of the linear alkyl aromatic columns.

The catalysts used in the first and second reaction zones can be the same or different. The reaction zones can use solid catalyst beds; alternatively, liquid phase alkylation can be used in one or both reactions zones. Suitable liquid phase catalysts include, but are not limited to hydrofluoric acid and sulfuric acid.

The catalyst for the second reaction zone desirably has large pore sizes which are suitable for the formation of dialkylbenzenes, while limiting the formation of trialkylbenzenes. The pore size is typically at least about 7.4 Å or more.

Typically, the catalysts are acidic. Preferred alkylation catalysts comprise zeolites having a zeolite framework type selected from the groups consisting of beta, MOR, MWW, FAU and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. The MOR, MWW, FAU, NES, and other zeolite framework types are described in Ch. Baerlocher, W. M. Meier and D. H. Olson, "Atlas of Zeolite Framework Types," 5th Ed., Elsevier: Amsterdam, 2001, herein incorporated by reference. The FAU and UZM-8 molecular sieves may have any convenient particle size. Often the particle sizes of the molecular sieves range upwards of 5 microns or more in major dimension, for example, about 50 to 5000 nanometers in major dimension. Particle sizes in the lower portion of the range are sometimes preferred as the coproduction of heavies may be reduced. Major particle dimensions of less than about 500, e.g., from about 50 to 300, nanometers are often desirable. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1.

Newer alkylation catalysts can also be used in this process. For example, one such catalyst comprises a mixture of two types of zeolitic materials, where the zeolites are mixed and produced to have two zeolites within a single catalyst pellet. With the new catalysts, the first zeolite is also characterized by its acidity, wherein the acidity is characterized by having less than 70% of $NH_3$ desorption off the zeolite at temperatures greater than 400° C. The $NH_3$-TPD experimental procedure comprises: calibration of the NH.sub.3-TPD system with 5 injections of 0.2 cc pulses of $NH_3$ at 2 minute intervals into a flow of UHP grade helium at 40 cc/minute. The data collected from the Thermal Conductivity Detector is integrated and used to calibrate the detector response to a known quantity of $NH_3$. An equilibrated sample, for moisture content is weighed at approximately 250 mg and placed in the reactor. The sample is pretreated in a flow of 20% $O_2$/He UHP grade at a rate of 100 cc/minute and with a temperature ramp of 10° C./minute up to a maximum temperature of 650° C. The sample is held at this temperature for one hour, and purged with UHP grade helium for 15 minutes and cooled to the saturation temperature. The pretreatment is for removal of water and residual contaminants. The sample is saturated with anhydrous $NH_3$ at 150° C. using multiple pulses of $NH_3$ injected into He flowing at 40 cc/min. The minimum quantity of $NH_3$ used to saturate the sample is 50 cc. The excess ammonia is purged from the sample in flowing (40 cc/min) UHP grade helium for about 8 hours. The $NH_3$ is desorbed from the sample in a flow (40 cc/min) of UHP grade helium with a temperature ramp of 10° C./minute to a final temperature of about 605° C. All gases have been purified using appropriate gas purifiers. The $NH_3$ desorbed is detected with a Thermal Conductivity Detector. The detector response is converted to moles of $NH_3$ using the detector response obtained at the beginning of the experiment. The integrated results are reported by integration of the temperature range of interest and reported as mmoles $NH_3$/g sample. An example of the first zeolite is UZM-8.

The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage. The reduced acidity and reduced space significantly suppresses the isomerization and cracking pathways, while the leaving the primary alkylation reaction unaffected. This decreases the undesired side reactions that reduce the amount and quality of the LAB product. This is contrary to what one would expect, as it has been found that incorporating or leaving some alkali or alkaline earth cations in the catalyst significantly improves the catalyst performance. This is especially true with respect to the performance around the linearity of the alkylbenzene, and the retention of linearity as the operating temperatures are increased. Normally, the alkali or alkaline earth cations are removed because without the rare earth exchange, the alkali or alkaline earth cations are detrimental to the catalyst life and regenerability.

Suitable catalysts include, but are not limited to, fluorocarbon sulfonic acid, fluoride amorphous silica alumina, sulfate zirconia, UZM-8, rare earth substituted-X zeolite, rare earth substituted-Y zeolite, or combinations thereof.

The following description of the alkylation reaction zone applies to either or both reaction zones.

The alkylation reaction zone may contain at least 2, or at least 3, and most frequently between about 3 and 10, reaction zones in series to which a portion of the aliphatic feedstock is fed. Often a trim alkylation reaction zone follows the series to react residual olefin in the effluent from the last reaction zone in series. The reaction zones may be in a common vessel or in separate vessels. The reaction zones may be the same or different sizes. Additional reaction zones may be used in parallel.

The number of reaction zones in series will be related to the overall aromatic compound to aliphatic feed ratio desired and to the desired Reaction Zone Delta T. For example, for a given ratio, more reaction zones will be required to achieve a given Reaction Zone Delta T than for a higher Reaction Zone Delta T.

A heat exchanger may be provided between each of the reaction zones in the series. If desired, a heat exchanger can be provided immediately upstream of any trim reaction zone, but the use of such a heat exchanger is not required. As used herein, a heat exchanger is a unit operation which provides controlled cooling of the effluent from the preceding reaction zone by direct, indirect, or a combination thereof heat exchange and does not refer to ambient heat loss. The amount of cooling to be effected between each reaction zone can be varied widely. Generally, the cooling is at least sufficient to remove at least about 75 percent of the heat generated in the preceding reaction zone. The cooled effluent is often at a temperature at least 5° C., and sometimes between 5° C. and 20° C., lower than the temperature of the effluent fed to the heat exchanger. Often the cooling is sufficient to provide the effluent at substantially the same temperature as the feed to the preceding reaction zone. In one embodiment, the cooling of the effluent is sufficient to reduce the temperature of the effluent by a least an amount of 60 percent of the Reaction Zone Delta T of the reaction zone producing the effluent. Thus, the cooling counters the Reaction Zone Delta T of the preceding reaction zone.

A portion of the aliphatic feed is fed to each of the reaction zones in the series. Advantageously, this feed can be cooler than the preceding reaction zone effluent and serves to provide direct heat exchange. Alternatively or in addition, indirect heat exchange can be used to reduce the temperature of the effluent. The cooling medium for the indirect heat exchange may be water or any conveniently available, cooler process fluid.

The optional trim reaction zone typically assures that at least about 99, preferably at least about 99.5, mole percent of the olefin is reacted. In one preferred embodiment, substantially all of the olefin contained in the zone effluent that is passed to the trim reaction zone is consumed.

The effluent from the last reaction zone (or trim reaction zone if used) is directly passed to the refining system. The alkylbenzene refining system serves to remove aromatic compound, olefins, heavies, and, if present, paraffins, from the alkylated product.

The separation zones comprise a first distillation unit that recovers essentially all the benzene from the first alkylation effluent and provides a relatively pure benzene stream as the overhead. The bottoms stream from the first distillation unit is mixed with the second part of the feed stream and sent to the second alkylation reaction zone. The effluent from the second alkylation zone is then passed to a second distillation unit to separate paraffins and unreacted olefins as the overhead. The bottoms from this second distillation unit contains dialkylbenzene and, in some cases, monoalkylbenzene as well. If the monoalkylbenzene to olefin ratio in the second reactor is stoichiometric or near stoichiometric, then the bottoms from the second distillation unit is the dialkylbenzene product. If the monoalkylbenzene to olefin ratio in the second reactor is greater than stoichiometric, the bottoms will contain both dialkylbenzene and monoalkylbenzene. In this situation, there can be an optional heavy alkylate distillation column for the bottoms stream to separate the dialkylbenzene from the monoalkylbenzene.

In further detail for purposes of illustration, the benzene distillation is generally conducted with a bottoms temperature of less than about 300° C., preferably less than about 275° C., usually between about 230° C. and 270° C., and at a pressure at which the overhead is provided of between about 5 and 300, preferably between about 35 and 70, kPa gauge. The overhead generally contains less than about 2, preferably less than about 1.5, weight percent paraffins. The benzene distillation assembly may comprise one or more distillation columns. More than one overhead may be obtained from the benzene distillation assembly. For instance, a highly pure stream may be obtained for process needs such as regenerating catalysts or sorbents, e.g., having a paraffin concentration less than about 1, preferably less than about 0.1, weight percent. A lesser purity overhead may be obtained from the benzene distillation assembly, e.g., as a side draw, for use as a recycle to the alkylation reaction.

Each column used for benzene distillation may contain any convenient packing or distillation trays, but most often trays such as sieve and bubble trays, are used.

Often the assembly provides at least about 5 theoretical plates, for example, 6 to 70, or 20 to 50. The reflux ratio is often in the range of about 2:1 to 1:10, or about 1.5:1 to 1:5. The bottoms stream from the benzene distillation generally contains less than about 1000 ppmw, or less than about 50 ppmw, and sometimes less than about 5 ppmw, benzene. The benzene distillation may occur in a single column or two or more distinct columns may be used. For instance, a stripping column may be used to remove a portion, e.g., 20 to 50 percent, of the benzene and then the bottoms from the stripping column would be subjected to rectification in a subsequent column to obtain the desired separation.

The paraffin distillation is generally conducted with a bottoms temperature of less than about 300° C., or less than about 275° C., usually between about 250° C. and 275° C., and at a pressure at which overhead is provided of between about 5 and 110 kPa absolute, or between about 10 and 50 kPa absolute. The column may contain any convenient packing or distillation trays, but most often sieve trays are used. Often the paraffins distillation assembly provides at least about 5 theoretical plates, or about 7 to about 20. The reflux ratio is often in the range of about 3:1 to 1:10, or about 1:1 to 1:3. The bottoms stream from the paraffins distillation generally contains less than about 5000, or less than about 500, parts by million by weight (ppmw) paraffins and less than about 10, often less than about 1, ppmw benzene.

The paraffins distillation may occur in a single column, or two or more distinct columns may be used.

The heavy alkylate distillation is generally conducted with a bottoms temperature of less than about 300° C., or less than about 275° C., usually between about 250° C. and 275° C., and at a pressure of between about 0.5 and 30 kPa absolute, or between about 1 and 5, kPa absolute. The column may contain any convenient packing or distillation trays, but most often structured packing is used. Often the heavy alkylate distillation assembly provides at least about 5 theoretical plates, for example 10 to 30, or 10 to 20. The reflux ratio is often in the range of about 2:1 to 1:5, or about 0.2:1 to 1:1. The overhead from the heavy alkylate distillation generally contains less than about 1000, or less than about 100 ppmw, and sometimes less than about 50 ppmw, total heavies.

The refining system may contain additional distillation zones, e.g., to recover additional alkylbenzene from heavies.

EXAMPLE

The feed contains 64,830 paraffins and 8841 olefins by weight. The system uses two reaction zones with an amorphous fluoride silica-alumina catalyst (UOP Da-114 catalyst) for the first reactor and zeolitic Detal alkylation catalyst (UOP ZDA-2 catalyst) in the second reactor. The feed is split into two portions: the first (51.2%) containing 33,219 paraffins and 4,530 olefins, and the second (48.8%) containing 31,611 paraffins and 4,311 olefins. The benzene stream contains 63,656 benzene. The effluent from the first reaction zone contains 33,219 paraffins, 0 olefins, 61,541 benzene, 6,373 linear monoalkylbenzenes, and 272 heavy alkylbenzenes, which are primarily dialkylbenzenes. After separation of the benzene from the other components, and mixing the second portion of the feed with the other components from the separation, the feed contains 64,830 paraffins, 4,311 olefins, 0 benzene, 6,373 monoalkylbenzenes, and 272 dialkylbenzenes. The mixed feed is sent to the second reaction zone. The effluent from the second reaction zone contains 64,830 paraffins, 0 olefins, 0 benzene, 0 monoalkylbenzenes, and 10,956 dialkylbenzenes. The concentration of dialkylbenzenes is 14.5%, which is low enough to prevent rapid deactivation of the catalyst during operation.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A continuous process for the production of dialkylbenzene comprising:

contacting benzene, and a first feed comprising a first olefin and a first component in a first alkylation reaction zone under alkylation conditions in the presence of a first alkylation catalyst comprising an amorphous fluoride silica-alumina to produce a first effluent containing monoalkylbenzene and unreacted benzene, wherein the weight ratio of the first component to the first olefin is at least 3:1;

separating the monoalkylbenzene from the first effluent;
recycling at least a portion of the unreacted benzene to the first reaction zone;
contacting the monoalkylbenzene with a second feed comprising a second olefin and a second component in a second alkylation reaction zone under alkylation conditions in the presence of a second alkylation catalyst comprising a first zeolite comprising UZM-8 zeolite and second zeolite comprising a rare earth substituted X zeolite, Y zeolite or a zeolite having an EMT/FAU intergrowth, wherein the first and second zeolites are intermingled into a single catalyst particles to produce a second effluent containing dialkylbenzene, wherein the weight ratio of the second component to the second olefin is at least 3:1; and
separating the dialkylbenzene from the second effluent;
wherein the first olefin, the second olefin, or both are either $C_{10}$ to $C_{13}$ olefins or $C_{14}$ to $C_{17}$ olefins, and the first component and the second component are either $C_{10}$ to $C_{13}$ paraffins or $C_{14}$ to $C_{17}$ paraffins, but are the different molecular weight range from the olefins.

2. The process of claim 1 wherein the second effluent further comprises unreacted second component, and further comprising recycling at least a portion of the unreacted second component to the second alkylation reaction zone.

3. The process of claim 1 wherein the second effluent further comprises unreacted monoalkylbenzene, and further comprising recycling the unreacted monoalkylbenzene to the second alkylation reaction zone.

4. The process of claim 1 wherein a ratio of the monoalkylbenzene to the olefin in the second alkylation reaction zone is in a range of about 1:1 to about 2:1.

* * * * *